United States Patent
Laviano et al.

(10) Patent No.: US 10,456,145 B2
(45) Date of Patent: Oct. 29, 2019

(54) EXPANDABLE REAMERS

(71) Applicant: ARTHREX, INC., Naples, FL (US)

(72) Inventors: Anthony Laviano, Fort Myers, FL (US); Thomas E. Anstead, Naples, FL (US); John Gualdoni, Naples, FL (US)

(73) Assignee: ARTHREX, INC., Naples, FL (US)

( * ) Notice: Subject to any disclaimer, the term of this patent is extended or adjusted under 35 U.S.C. 154(b) by 156 days.

(21) Appl. No.: 15/596,309

(22) Filed: May 16, 2017

(65) Prior Publication Data

US 2018/0333160 A1  Nov. 22, 2018

(51) Int. Cl.
*A61B 17/16* (2006.01)

(52) U.S. Cl.
CPC ...... *A61B 17/1615* (2013.01); *A61B 17/1633* (2013.01)

(58) Field of Classification Search
CPC ............ A61B 17/1615; A61B 17/1617; A61B 17/1624; A61B 17/1633
See application file for complete search history.

(56) References Cited

U.S. PATENT DOCUMENTS

| | | |
|---|---|---|
| 3,702,611 A | 11/1972 | Fishbein |
| 6,383,188 B2 * | 5/2002 | Kuslich .............. A61B 17/1617 408/158 |
| 6,746,451 B2 | 6/2004 | Middleton et al. |
| 7,036,611 B2 | 5/2006 | Radford et al. |
| 7,909,827 B2 | 3/2011 | Reiley et al. |
| RE42,757 E | 9/2011 | Kuslich et al. |
| 8,246,627 B2 | 8/2012 | Vanleeuwen et al. |
| 8,343,158 B2 | 1/2013 | Birkbeck |
| 8,926,615 B2 | 1/2015 | Ek |
| 9,028,499 B2 | 5/2015 | Keyak et al. |
| 9,084,615 B2 | 7/2015 | Cleveland et al. |
| 2004/0097947 A1 | 5/2004 | Wolford et al. |
| 2005/0113836 A1 | 5/2005 | Lozier et al. |
| 2005/0240193 A1 | 10/2005 | Layne et al. |
| 2005/0277971 A1 | 12/2005 | Melkent et al. |
| 2006/0057184 A1 | 3/2006 | Nycz et al. |
| 2006/0241629 A1 | 10/2006 | Krebs et al. |
| 2008/0114364 A1 | 5/2008 | Goldin et al. |
| 2011/0238074 A1 | 9/2011 | Ek |
| 2012/0004594 A1 | 1/2012 | Schulz et al. |
| 2012/0209274 A1 | 8/2012 | Belaney et al. |
| 2012/0271357 A1 | 10/2012 | Arthur et al. |
| 2014/0046330 A1 | 2/2014 | Goldin et al. |

(Continued)

FOREIGN PATENT DOCUMENTS

| | | |
|---|---|---|
| CN | 202288427 U | 7/2012 |
| EP | 2823778 A1 | 1/2015 |

(Continued)

OTHER PUBLICATIONS

International Search Report and Written Opinion of the International Searching Authority for Application No. PCT/US2018/031726 dated Dec. 4, 2018.

(Continued)

*Primary Examiner* — Anu Ramana
(74) *Attorney, Agent, or Firm* — Carlson, Gaskey & Olds

(57) ABSTRACT

An expandable reamer includes, inter alia, an outer tube, an inner shaft, a movable blade, and an actuator assembly. The expandable reamers can be used to remove diseased bone.

20 Claims, 16 Drawing Sheets

(56) References Cited

U.S. PATENT DOCUMENTS

| | | |
|---|---|---|
| 2014/0257297 A1 | 9/2014 | Koogle, Jr. et al. |
| 2014/0276831 A1 | 9/2014 | Zider et al. |
| 2014/0288561 A1 | 9/2014 | Tallarida et al. |
| 2015/0257771 A1 | 9/2015 | Cleveland et al. |

FOREIGN PATENT DOCUMENTS

| | | |
|---|---|---|
| EP | 2959850 A1 | 12/2015 |
| WO | 01/60268 A1 | 8/2001 |
| WO | 2014/089198 A1 | 6/2014 |

OTHER PUBLICATIONS

Advanced Core Decompressiuon System, Wright Medical Technology, Inc.

\* cited by examiner

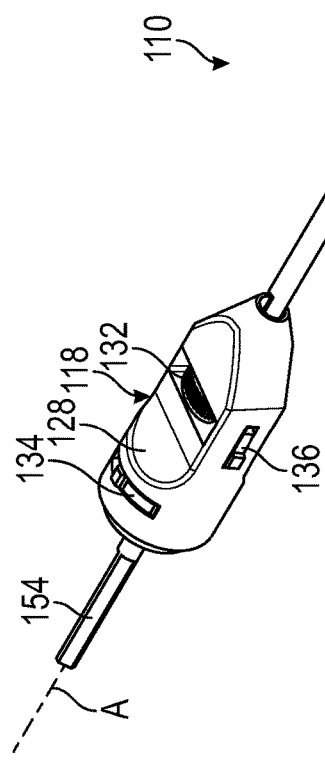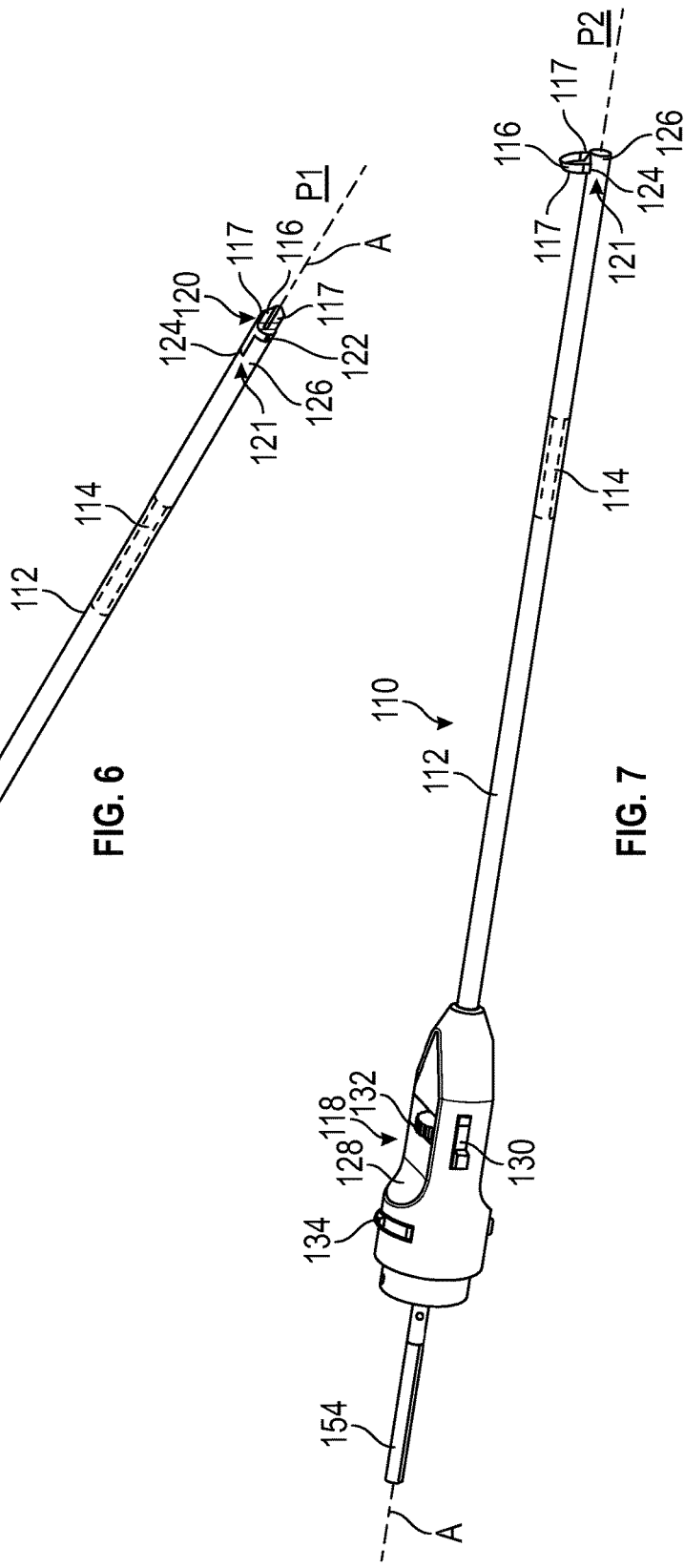

EXPANDABLE REAMERS

BACKGROUND

This disclosure relates to expandable reamers that can be introduced into a bone tunnel for removing diseased bone.

Diseased areas of bone may need to be removed from patients suffering from bone degeneration. For example, treating avascular necrosis (AVN) of the hip or osteochondritis dissecans (OCD) of the knee requires removing diseased bone from the patient. Various surgical cutting devices have been used for this purpose. However, advancements in this field of technology are desired for improving the procedure for removing diseased bone.

SUMMARY

This disclosure relates to expandable reamers that can be used to remove diseased bone. The expandable reamers include a blade that can be advanced to form a socket in bone. The blade is non-deployed as the expandable reamers are positioned relative to the diseased bone, and the blade is then deployed to a cutting position for removing the diseased portions of the bone.

According to an exemplary aspect of this disclosure, an expandable reamer includes, inter alia, an outer tube, an inner shaft within the outer tube, a blade hinged to the inner shaft and movable between a first position in which the blade is inside the outer tube and a second position in which the blade is exposed outside of the outer tube, and an actuator assembly configured to move the blade between the first position and the second position. The actuator assembly includes a selector sleeve, an actuator, and a first pin movable within a helical groove of the actuator to linearly translate either the inner shaft or the outer tube as the selector sleeve is rotated. A ratcheting assembly includes an engaged position in which the selector sleeve is prevented from rotating and a disengaged position in which the selector sleeve is free to rotate. A pawl of the ratcheting assembly engages a gear in the engaged position and is released from the gear in the disengaged position According to another exemplary aspect of this disclosure, an expandable reamer includes, inter alia, an outer tube, an inner shaft within the outer tube, a blade movable between a first position in which the blade is inside the outer tube and a second position in which the blade is exposed outside of the tube, and an actuator assembly configured to move the blade between the first position and the second position. The actuator assembly includes a selector sleeve, an actuator, and a first pin movable within a groove of the actuator to linearly translate either the inner shaft or the outer tube as the selector sleeve is rotated.

A method for removing diseased bone includes, inter alia, positioning an expandable reamer relative to diseased bone with a blade of the expandable reamer positioned in a non-cutting position, and incrementally advancing the blade to a cutting position relative to the diseased bone by rotating a selector sleeve of the expandable reamer. As the selector sleeve is rotated, a pin of the selector sleeve travels within a groove of an actuator to linearly translate the actuator.

BRIEF DESCRIPTION OF THE DRAWINGS

The drawings that accompany the detailed description can be briefly described as follows:

FIGS. 6 and 7 illustrate an expandable reamer according to a second embodiment of this disclosure.

DETAILED DESCRIPTION

Figure 1:
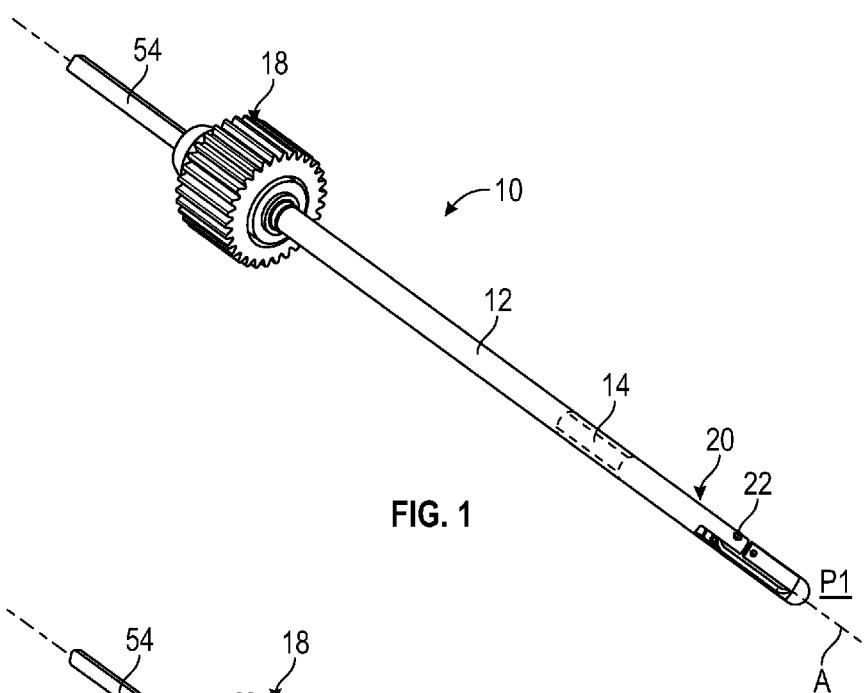
FIGS. 1 and 2 illustrate an expandable reamer according to a first embodiment of this disclosure.
Figure 2:
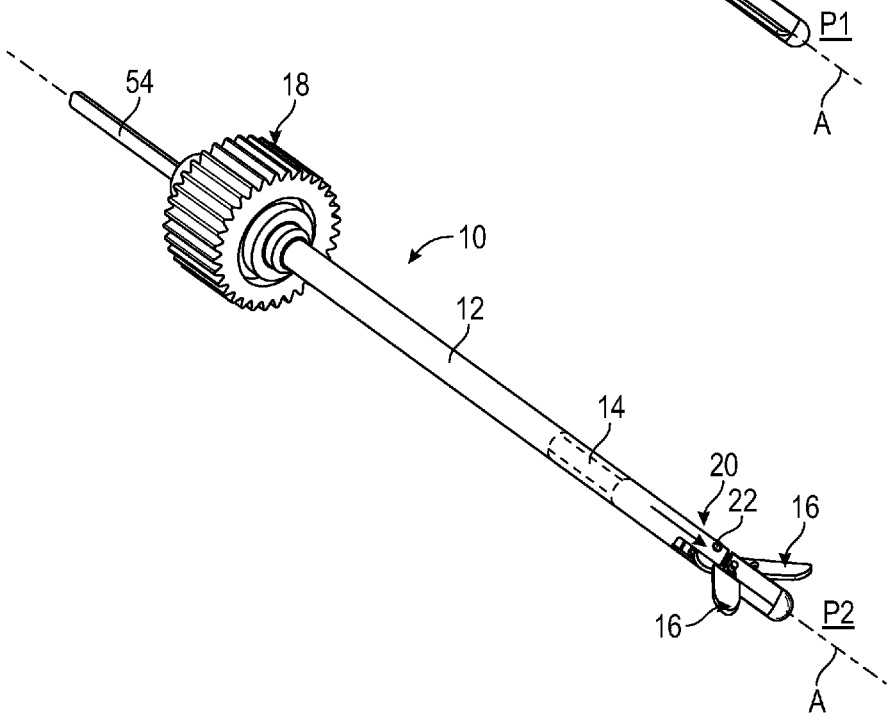

This disclosure describes expandable reamers that can be used to remove diseased bone. The expandable reamers include at least one blade that can be incrementally advanced to form a socket in bone. The blade is held in a non-cutting positon as the expandable reamers are positioned relative to the diseased bone, and the blade is then deployed to a cutting position for removing the diseased portions of the bone.

According to an exemplary aspect of this disclosure, an expandable reamer includes, inter alia, an outer tube, an inner shaft within the outer tube, a blade hinged to the inner shaft and movable between a first position in which the blade is inside the outer tube and a second position in which the blade is exposed outside of the outer tube, and an actuator assembly configured to move the blade between the first position and the second position. The actuator assembly includes a selector sleeve, an actuator, and a first pin movable within a helical groove of the actuator to linearly translate either the inner shaft or the outer tube as the selector sleeve is rotated. A ratcheting assembly includes an engaged position in which the selector sleeve is prevented from rotating and a disengaged position in which the selector sleeve is free to rotate. A pawl of the ratcheting assembly engages a gear in the engaged position and is released from the gear in the disengaged position.

According to another exemplary aspect of this disclosure, an expandable reamer includes, inter alia, an outer tube, an inner shaft within the outer tube, a blade movable between a first position in which the blade is inside the outer tube and a second position in which the blade is exposed outside of the tube, and an actuator assembly configured to move the blade between the first position and the second position. The actuator assembly includes a selector sleeve, an actuator, and a first pin movable within a groove of the actuator to linearly translate either the inner shaft or the outer tube as the selector sleeve is rotated.

According to another exemplary aspect of this disclosure, an expandable reamer includes, inter alia, an outer tube, an inner shaft within the outer tube, a blade movable between a first position in which the blade is inside the outer tube and a second position in which the blade is exposed outside of the tube, and an actuator assembly configured to move the blade between the first position and the second position. The actuator assembly includes a selector sleeve, an actuator, and a first pin movable within a groove of the actuator to linearly translate either the inner shaft or the outer tube as the selector sleeve is rotated.

In a further embodiment, a cam cap is configured to guide movement of a blade outwardly of an outer tube.

In a further embodiment, a cam cap is positioned within a distal portion of an outer tube.

In a further embodiment, a cam cap includes a slanted wall that guides a blade along an arced path as the blade is moved between a first position and a second position.

In a further embodiment, a cam cap includes grooved tracks disposed on each side of a slanted wall, and a blade includes projections that are guided within the grooved tracks.

In a further embodiment, a blade is hinged to a distal portion of an inner shaft.

In a further embodiment, a groove is a helical groove.

In a further embodiment, a helical groove includes a plurality of detents.

In a further embodiment, a first pin is movable from a first detent to a second detent to alter a cutting diameter of a blade.

In a further embodiment, a ridge is disposed between a first detent and a second detent of an actuator.

In a further embodiment, a ratcheting assembly locks a selector sleeve from rotational movement.

In a further embodiment, a ratcheting assembly includes an engaged position in which a selector sleeve is prevented from rotating and a disengaged position in which the selector sleeve is free to rotate.

In a further embodiment, a ratcheting assembly includes a pawl and a gear, and the pawl engages the gear in the engaged position and is released from the gear in the disengaged position.

In a further embodiment, a selector sleeve is movable longitudinally forward to move the ratcheting assembly from an engaged position to a disengaged position.

In a further embodiment, an outer tube and an inner shaft are disposed along a longitudinal axis, and a blade is parallel to the longitudinal axis in a first position and transverse to the longitudinal axis in a second position.

A method for removing diseased bone according to another exemplary aspect of this disclosure includes, inter alia, positioning an expandable reamer relative to diseased bone with a blade of the expandable reamer positioned in a non-cutting position, and incrementally advancing the blade to a cutting position relative to the diseased bone by rotating a selector sleeve of the expandable reamer. As the selector sleeve is rotated, a pin of the selector sleeve travels within a groove of an actuator to linearly translate the actuator.

In a further embodiment, a method includes rotating an expandable reamer with a blade in a cutting position to remove diseased bone.

In a further embodiment, a method includes reaming a tunnel into a bone that includes diseased bone prior to positioning an expandable reamer.

In a further embodiment, a method includes backfilling a bone tunnel with a biologic after removing diseased bone. A biologic includes, inter alia, bone marrow aspirate, bone marrow concentrate, platelet rich plasma, bone morphogenetic proteins (e.g., BMP-2), demineralized bone matrix, growth factors (e.g., TGF-β), autologous or allogeneic ex vivo cultured bone marrow cells, and the like, and combinations thereof.

In another embodiment, a method includes backfilling a bone tunnel with a bone cement after removing diseased bone. Bone cements are known and include, inter alia, calcium phosphate cements (CPC). Bone cements can have varying formulations to provide different characteristics and can be injectable. In an example, a nanocrystalline calcium phosphate formulation can be mixed with saline and implanted in a bone tunnel where the formulation hardens and converts to nanocrystalline hydroxyapatite. Specifically, a CPC can comprise tricalcium phosphate (e.g., α-TCP or β-TCP), tetracalcium phosphate, hydroxyapatite ($Ca_{10}(PO_4)_6(OH)_2$), fluoroapatite ($Ca_5(PO_4)_3F$), monocalcium phosphate monohydrate (MCPH), dicalcium phosphate dehydrate (DCPD), dicalcium phosphate anhydrous, calcium deficient apatite CDA), tricalcium silicate, and combinations thereof. CPC formulations will also commonly include polysaccharides, and salts and mixtures thereof. For example, common polysaccharides in CPC formulations include hydroxypropylmethylcellulose (HPMC) and carboxymethylcellulose (CMC). In an example formulation, a CPC comprises at least 70 wt % α-TCP. In an embodiment, a CPC comprises 88 wt % α-TCP, 10 wt % DCPD, and 2 wt % HPMC.

In a further embodiment, a method includes incrementally advancing a blade by moving the blade along an arced path to a position radially outward from an outer tube of an expandable reamer.

FIGS. 1-5 illustrate an exemplary expandable reamer 10. The expandable reamer 10 is an orthopedic surgical device that may be part of a surgical instrumentation set designed for removing diseased bone from a patient. In an embodiment, the expandable reamer 10 is used to treat avascular necrosis (AVN) of the hip. In another embodiment, the expandable reamer 10 is used to treat osteochondritis dissecans (OCD) of the knee. The expandable reamers described in this disclosure could be used for any surgical procedure that requires removing diseased bone in either human or animal patients.

The expandable reamer 10 may include an outer tube 12, an inner shaft 14, one or more blades 16, and an actuator assembly 18. The blades 16 may be incrementally advanced between a first position P1 (see FIG. 1) and a second position P2 (see FIG. 2). The first position P1 is a non-cutting position in which the one or more blades 16 are not exposed outside of the outer tube 12, and the second position P2 is a cutting position in which the one or more blades 16 are exposed outwardly of the outer tube 12 for removing diseased bone. In an embodiment, the one or more blades 16 are incrementally advanced to bore a socket into bone that is any diameter. In an embodiment, the diameter is a range between about 5 mm to about 10 mm, about 5 mm to about 15 mm, about 5 mm to about 18 mm, or about 5 mm to about 20 mm. Of course, the expandable reamer 10 could be configured to bore a socket of any size.

The outer tube 12 and the inner shaft 14 are disposed along a longitudinal axis A. The inner shaft 14 extends inside the outer tube 12 and is thus at least partially surrounded by the outer tube 12. In an embodiment, the outer tube 12 and the inner shaft 14 are concentric relative to one another.

In another embodiment, the inner shaft 14 is fixed and the outer tube 12 is movable along the longitudinal axis A of the expandable reamer 10. However, an opposite configuration is also contemplated in which the outer tube 12 is fixed and the inner shaft 14 moves along the longitudinal axis A.

Movement of either the inner shaft 14 or the outer tube 12 relative to the other of the inner shaft 14 and the outer tube 12 positions the one or more blades 16 in the second positions P2 for reaming diseased tissue, as discussed in greater detail below.

The expandable reamer 10 shown in FIG. 1 includes two blades 16. However, the expandable reamer 10 could include a single blade or greater than two blades within the scope of this disclosure.

Figure 3:
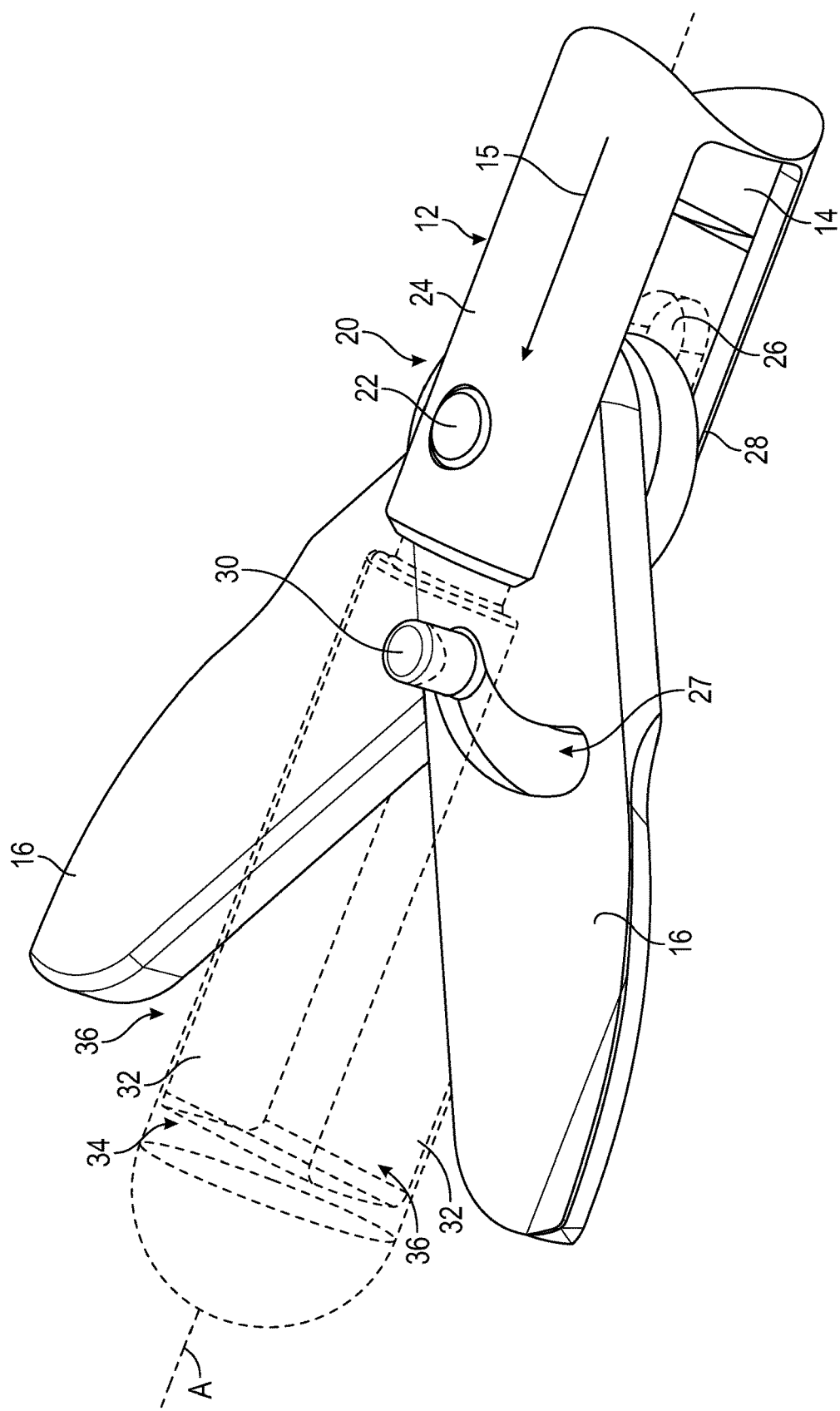
FIG. 3 is an enlarged view of a portion of the expandable reamer of FIGS. 1 and 2.

Referring to FIG. 3, the blades 16 may be attached near a distal portion 20 of the outer tube 12 by a first pin 22. In an embodiment, the first pin 22 extends through a first arm 24 of the distal portion 20 of the outer tube 12, then through both blades 16, then through a slot 26 formed in the inner shaft 14, and finally through a second arm 28 of the distal portion 20 of the outer tube 12. As the outer tube 12 is moved along the longitudinal axis A in the direction of arrow 15, the first pin 22 moves within the slot 26 of the inner shaft 14. This linear movement forces the blades 16 to push against a second pin 30, thereby moving the blades 16 radially outward from the outer tube 12 toward the second position P2. The second pin 30 may travel within a slot 27 of one of the blades 16 as the blades 16 are pushed against the second pin 30. In an embodiment, the second pin 30 extends between walls 32 of a cap 34 of the outer tube 12.

In an embodiment, the blades 16 are incrementally advanced through windows 36 that extend between the walls 32 of the cap 34 and between the first and second arms 24, 28 of the outer tube 12. Thus, in the first position P1, the expandable reamer 10 provides an atraumatic device that substantially reduces risks of inadvertent damage to surrounding tissue as the expandable reamer 10 is positioned within bone. The blades 16 of the expandable reamer 10 may be advanced radially outward from the outer tube 12 to the second position P2, or any position between the first position P1 and the second position P2, for preparing a socket in bone. In the second position P2, the blades 16 are non-parallel to the longitudinal axis A and are exposed outside of the outer tube 12.

Figure 4:
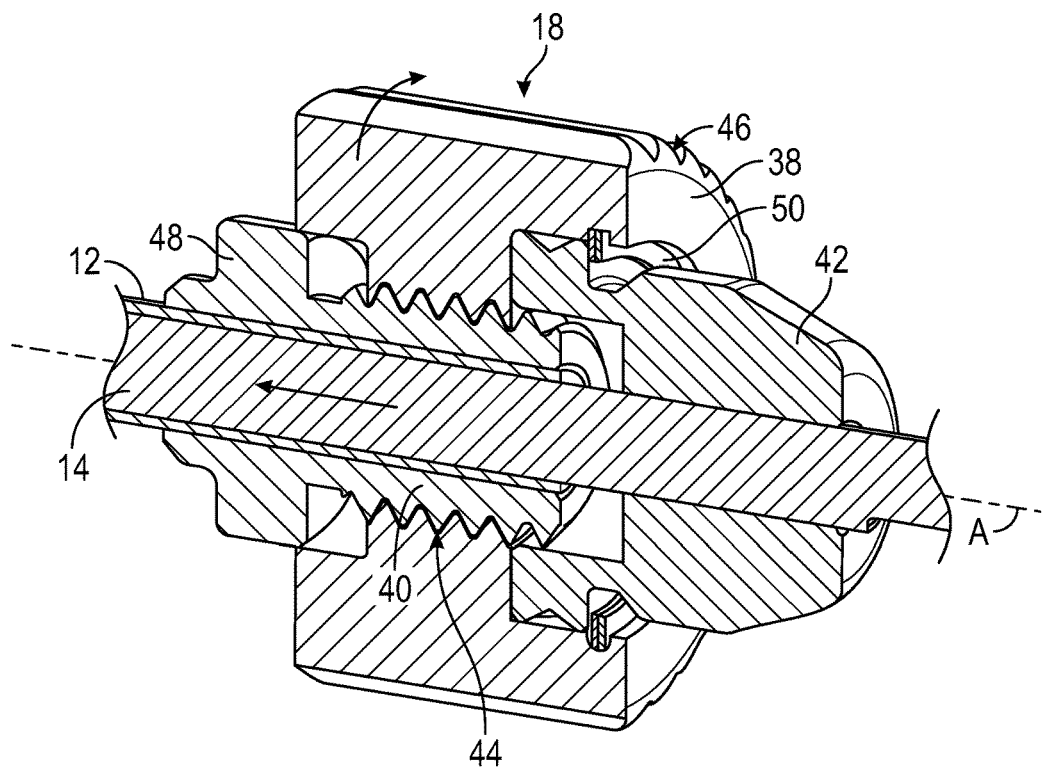
FIGS. 4 and 5 illustrate an actuator assembly of the expandable reamer of FIGS. 1 and 2.
Figure 5:
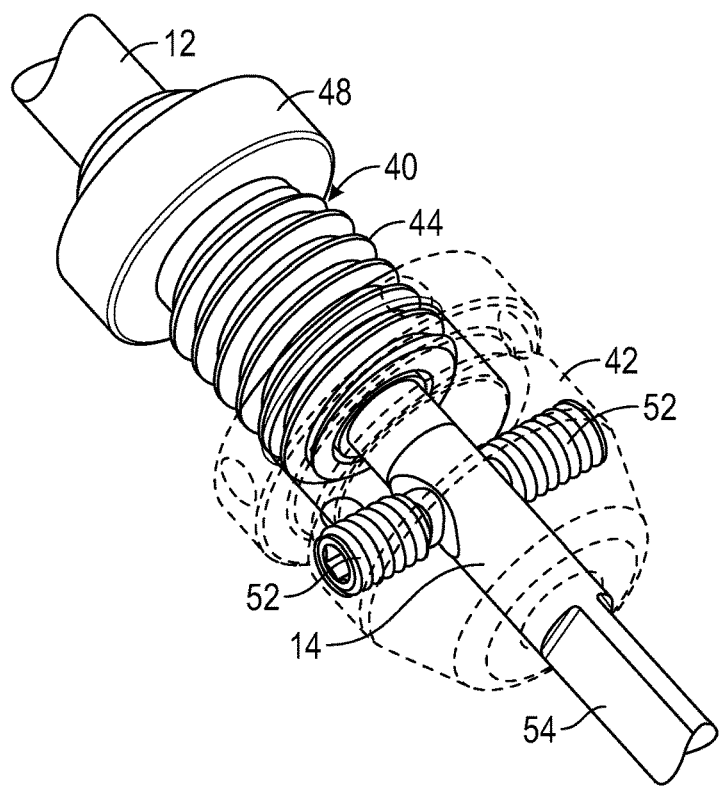
Figure 8:
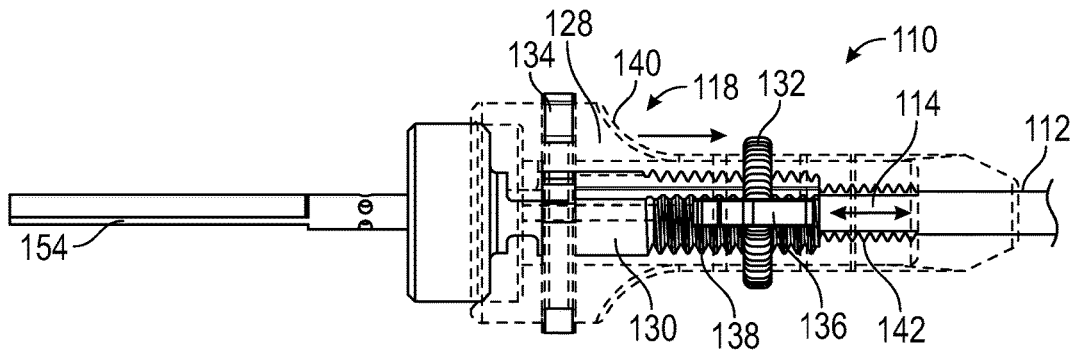
FIGS. 8, 9, and 10 illustrate an actuator assembly of the expandable reamer of FIGS. 6 and 7.
Figure 9:
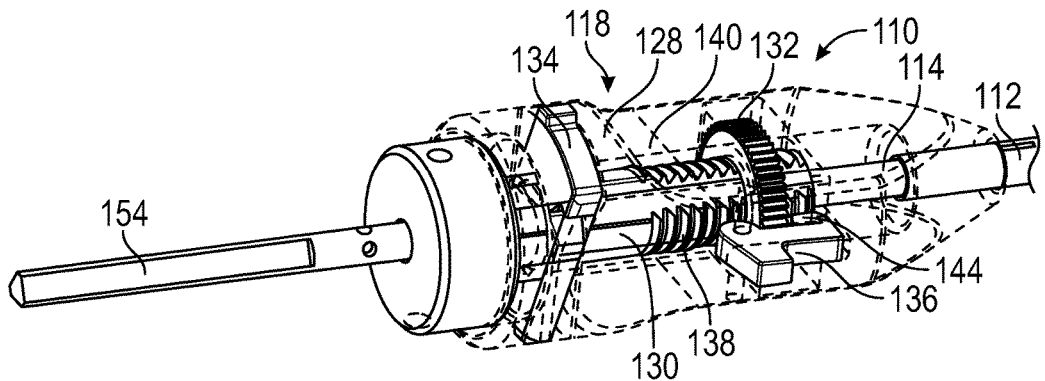
Figure 10:
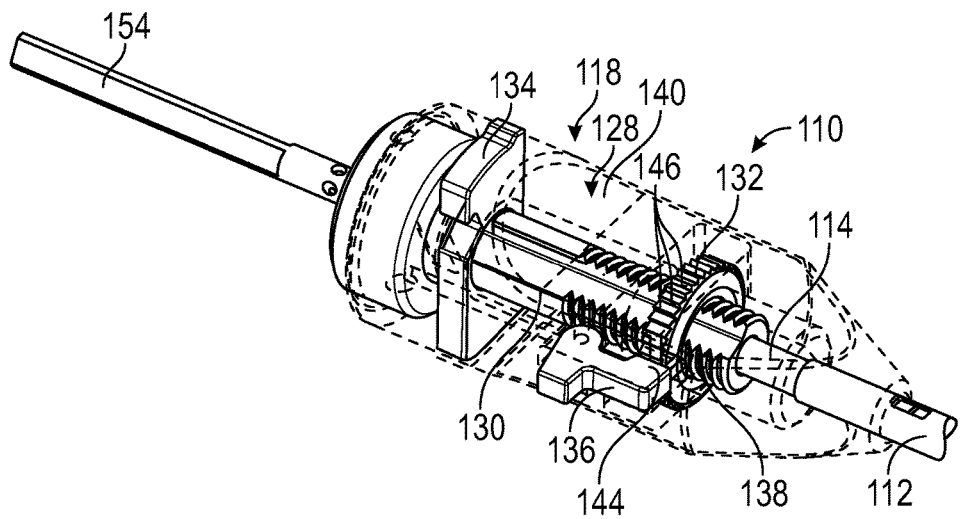
Figure 11:
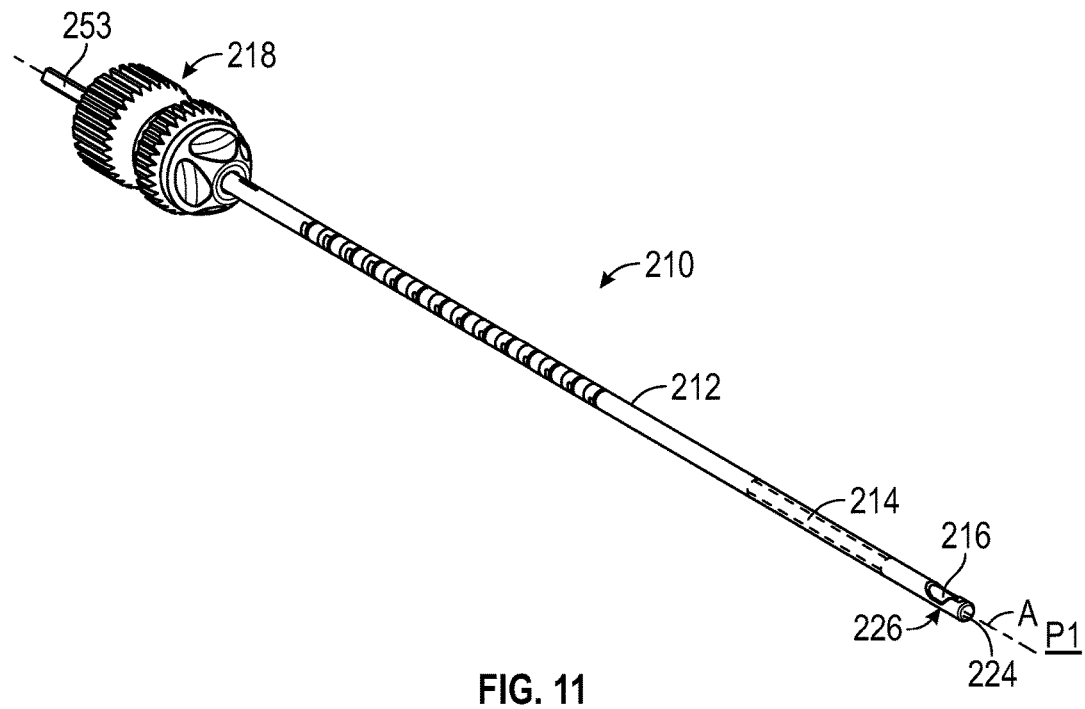
FIGS. 11 and 12 illustrate an expandable reamer according to a third embodiment of this disclosure.
Figure 12:
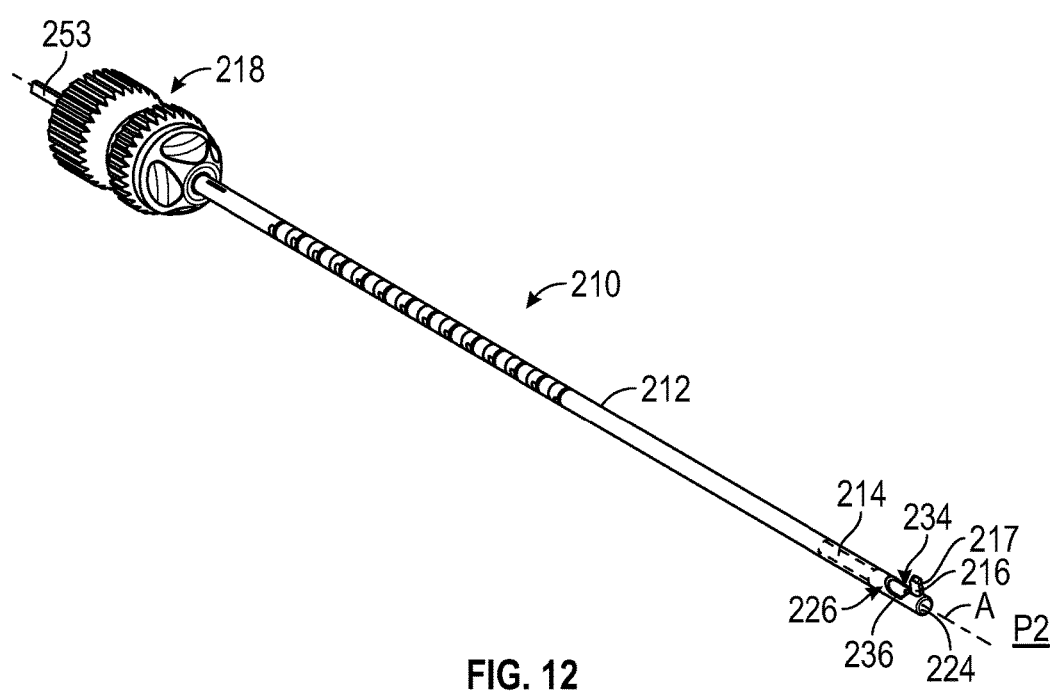

The actuator assembly 18 is configured for moving the blades 16 in the manner described above. As best illustrated in FIG. 4, the actuator assembly 18 may include a selector sleeve 38, an actuator 40, and a connector hub 42. The selector sleeve 38 is connected to the actuator 40, such as at a threaded connection 44. The selector sleeve 38 may be rotated relative to the connector hub 42 to linearly move the actuator 40 along the longitudinal axis A. In other words, rotational movement of the selector sleeve 38 translates the actuator 40 linearly.

The actuator 40 is connected (e.g., welded, etc.) to the outer tube 12, and therefore, in this example, linear movement of the actuator 40 results in linear movement of the outer tube 12. Linear movement of the outer tube 12 pushes the blades 16 against a second pin 30 in the manner described above and shown in FIG. 3 to move the blades toward the second position P2. Rotation of the selector sleeve 38 in the opposite direction retracts the blades 16 toward the first position P1.

The selector sleeve 38 may include a knurled surface 46. The knurled surface 46 is designed to improve a user's grip when turning the selector sleeve 38.

An extension 48 of the actuator 40 extends forward of the selector sleeve 38. The extension 48 supports the selector sleeve 38 and may provide a visual indication of the amount the blades 16 have been moved.

The connector hub 42 may be mounted relative to the selector sleeve 38 using a snap ring 50. In an embodiment, the connector hub 42 is connected to the inner shaft 14 via one or more set screws 52 (see FIG. 5).

The clutch assembly 18 may additionally include a connector 54. In an embodiment, the connector 54 is an integral component of the inner shaft 14. In another embodiment, the connector 54 is as a Jacobs connector. Powered equipment, such as a drill, may be connected to the connector 54 for rotating the entire expandable reamer 10 after the blades 16 have been positioned in the second position P2 to achieve a desired bore diameter in bone.

FIGS. 6-10 illustrate another exemplary expandable reamer 110. The expandable reamer 110 may include an outer tube 112, an inner shaft 114, a blade 116, and an actuator assembly 118. Using the actuator assembly 118, the blade 116 may be incrementally advanced between a first position P1 (see FIG. 6) and a second position P2 (see FIG. 7). The first position P1 is a non-cutting position in which the blade 116 is generally parallel to the outer tube 112, and the second position P2 is a cutting position in which the blade 116 is transverse to the outer tube 112.

The outer tube 112 and the inner shaft 114 are disposed along a longitudinal axis A. The inner shaft 114 extends inside the outer tube 112 and is thus at least partially surrounded by the outer tube 112. In an embodiment, the outer tube 212 is fixed and the inner shaft 114 moves along the longitudinal axis A. Movement of the inner shaft 114 relative to the outer tube 112 moves the blade 116 toward the second position P2 for reaming diseased tissue.

The expandable reamer 110 includes a single blade 116, although additional blades could be provided within the scope of this disclosure. In an embodiment, the blade 116 is movably connected to a distal portion 120 of the inner shaft 114 by a pin 122 (i.e., the blade 116 is hinged to the inner shaft 114). In another embodiment, the blade 116 includes one or more cutting edges 117 for cutting bone once positioned in the second position P2, or any position between the first and second positions P1, P2.

The blade 116 may be incrementally advanced (e.g., pivoted) through an opening 124 formed in the distal portion 121 of the outer tube 112 to create a retrograde socket in bone that can subsequently be backfilled with biologics. The opening 124 extends through a sidewall 126 of the outer tube 112, and the blade 116 may be moved radially outward of the outer tube 112 through the opening 124 of the sidewall 126.

The actuator assembly 118 is configured for pivoting the blade 116 between the first position P1 and the second position P2. The actuator assembly 118 may include a hub 128, an actuator 130, a depth stop dial 132, a release 134, and a lock 136.

The depth stop dial 132 may be rotated to a desired position on a threaded portion 138 of the actuator 130. This sets the diameter that is to be cut by the blade 116. The threaded portion 138 is located inside the hub 128, and the depth stop dial 132 extends inside the hub 128 but is partially exposed outside of the hub 128. The depth stop dial 132 can be rotated when the lock 136 is positioned in the unlocked position shown in FIG. 9.

The actuator assembly 110 may be positioned within a bone socket with the blade 116 in the first position P1. Once properly positioned, the release 134 may be actuated. This forces the hub 128 forward until a wall 140 of the hub abuts the depth stop dial 132. This action also activates a spring 142 (see FIG. 8) housed inside the hub 128 to force the inner shaft 114 forward, thus pivoting the blade 116 toward the second position P2.

The lock 136 may be actuated to lock the hub 128 and the depth stop dial 132 together. This may be done, for example, when using the expandable reamer 110 to ream a socket in bone. In the locked position, a pawl arm 144 of the lock 136 engages one or more notches 146 formed in the depth stop dial 132 (see FIG. 10).

The clutch assembly 118 may additionally include a connector 154. In an embodiment, the connector 154 is an integral component of the inner shaft 114. In another embodiment, the connector 154 is as a Jacobs connector. Powered equipment, such as a drill, may be connected to the connector 154 for rotating the entire expandable reamer 110 after the blade 116 has been positioned in the second position P2 to achieve a desired bore diameter in bone.

FIGS. 11-18 illustrate another exemplary expandable reamer 210. The expandable reamer 210 may include an outer tube 212, an inner shaft 214, a blade 216, and an actuator assembly 218. The blade 216 may be incrementally advanced between a first position P1 (see FIG. 11) and a second position P2 (see FIG. 12). The first position P1 is a non-cutting position in which the blade 216 is not exposed outwardly from the outer tube 212, and the second position P2 is a cutting position in which the blade 216 is exposed outwardly of the outer tube 212 for removing diseased bone. In an embodiment, the blade 216 may be incrementally advanced to bore a socket into bone that is any diameter (e.g., between about 5 mm to about 10 mm, about 5 mm to about 15 mm, about 5 mm to about 18 mm, or about 5 mm to about 20 mm). Of course, the expandable reamer 210 could be configured to bore a socket of any size.

The outer tube 212 and the inner shaft 214 are disposed along a longitudinal axis A. The inner shaft 214 extends inside the outer tube 212 and is thus at least partially surrounded by the outer tube 212. In an embodiment, the outer tube 212 and the inner shaft 214 are concentric relative to one another.

In another embodiment, the outer tube 212 is fixed and the inner shaft 214 moves along the longitudinal axis A. Movement of the inner shaft 214 relative to the outer tube 212 positions the blade 216 in the second position P2 for reaming diseased tissue, as discussed in greater detail below.

Figure 13:
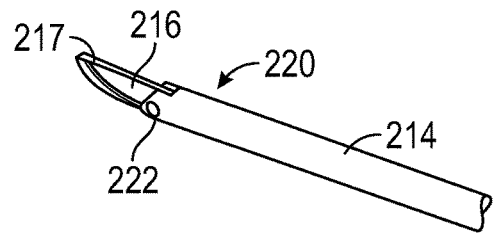
FIG. 13 illustrates a blade of the expandable reamer of FIGS. 11 and 12.

The expandable reamer 210 includes a single blade 216, although additional blades could be provided within the scope of this disclosure. In an embodiment, the blade 216 is movably connected to a distal portion 220 of the inner shaft 214 by a pin 222 (i.e., the blade 216 is hinged to the inner shaft 214 as best shown in FIG. 13). In another embodiment, the blade 216 includes one or more cutting edges 217 for cutting bone after the expandable reamer 210 has been positioned in the second position P2, or any position between the first and second positions P1, P2.

Figure 14:
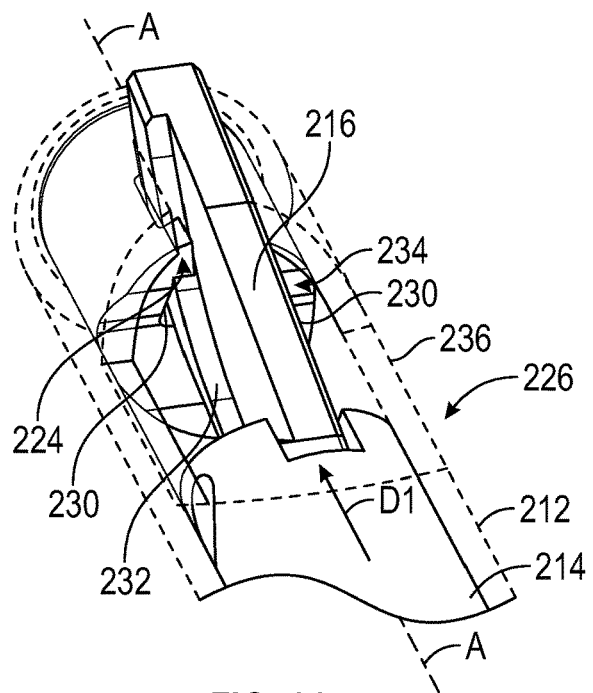
FIGS. 14 and 15 illustrate a cam cap of the expandable reamer of FIGS. 11 and 12.
Figure 15:
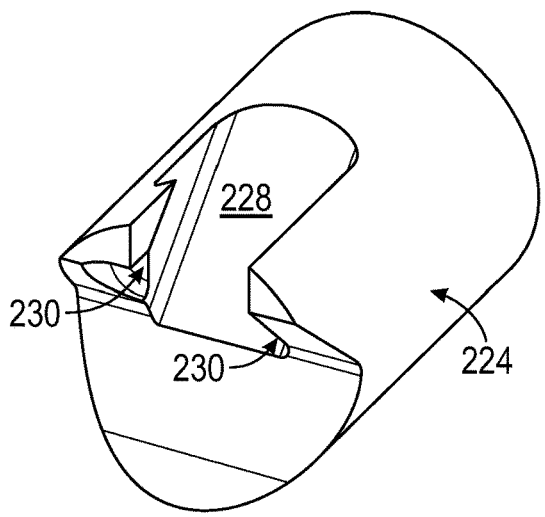

A cam cap 224 is received within a distal portion 226 of the outer tube 212 for guiding movement of the blade 216 between the first position P1 and the second position P2. In an embodiment, the cam cap 224 is press fit within the distal portion 226 of the outer tube 212. As best illustrated in FIGS. 14 and 15, for example, the cam cap 224 includes a slanted wall 228 and grooved tracks 230 positioned on each side of the slanted wall 228. The grooved tracks 230 are sized to receive projections 232 of the blade 216. As the inner shaft 214 is moved in a direction D1 along the longitudinal axis A, the projections 232 of the blade 216 are guided within the grooved tracks 230 of the cam cap 224. This movement causes the blade 216 to slide against the slanted wall 228, thus forcing the blade 216 along an arced path to a position that is radially outward of the outer tube 212. In an embodiment, the slanted wall 228 is positioned in a plane that is transverse to the longitudinal axis A.

In another embodiment, the blade 216 is incrementally advanced through a window 234 formed through a sidewall 236 of the outer tube 212. Thus, in the first position P1, the expandable reamer 210 provides an atraumatic device that substantially reduces risks of inadvertent damage to surrounding tissue as the expandable reamer 210 is positioned within bone. The blade 216 of the expandable reamer 210 may be advanced radially outward from the outer tube 212 to the second position P2 for preparing a socket in bone. In the second position P2, the blade 216 is non-parallel to the longitudinal axis A and is exposed outside of the outer tube 212.

Figure 16:
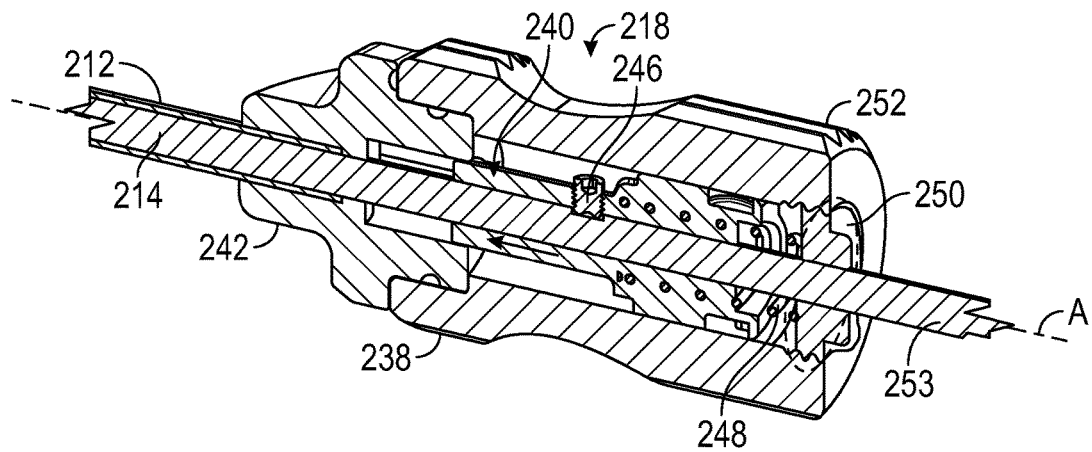
FIGS. 16, 17, and 18 illustrate an actuator assembly of the expandable reamer of FIGS. 11 and 12.
Figure 17:
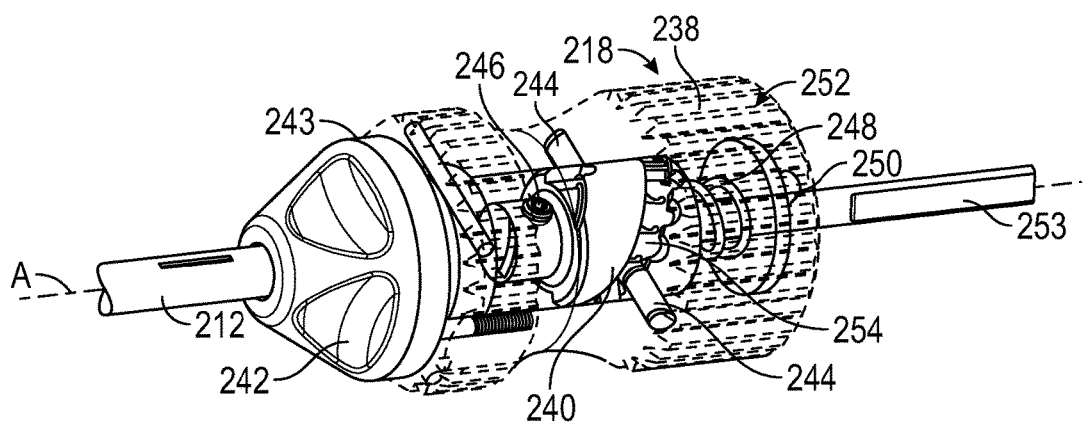
Figure 18:
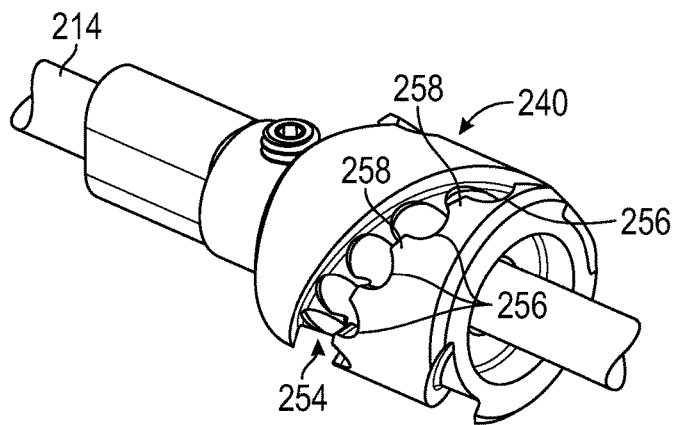
Figure 19:
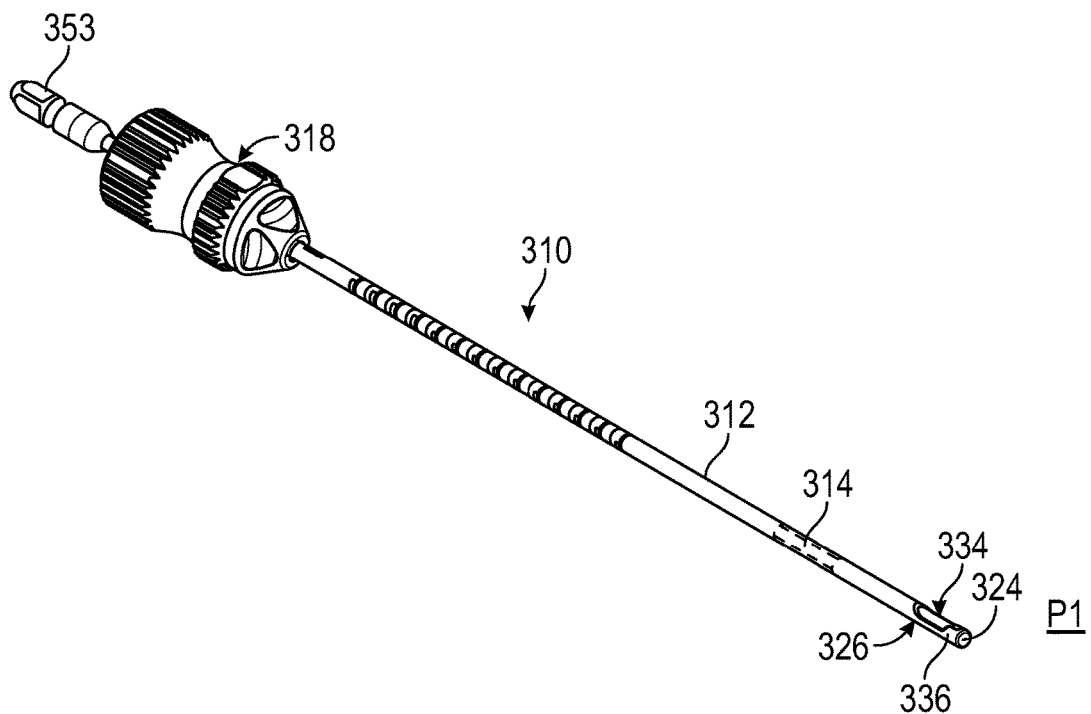
FIGS. 19 and 20 illustrate an expandable reamer according to a fourth embodiment of this disclosure.
Figure 20:
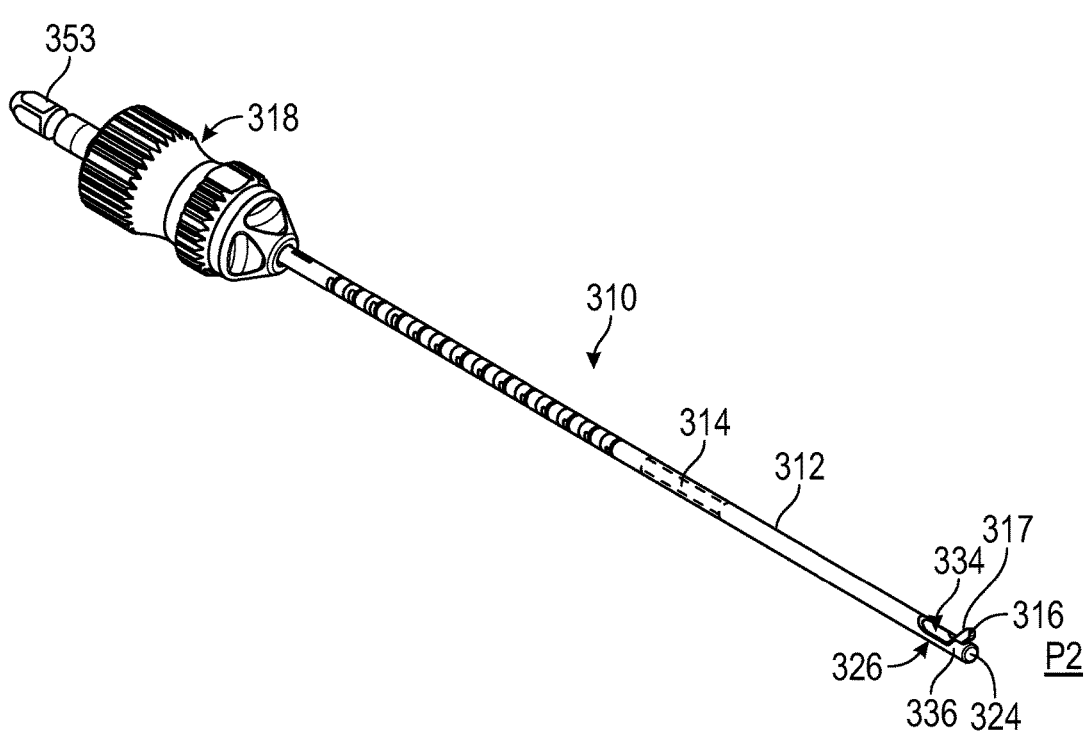

The actuator assembly 218 is configured for moving the blade 216 in the manner described above. As best illustrated in FIGS. 16-18, the actuator assembly 218 may include a selector sleeve 238, an actuator 240, and a hub 242. The selector sleeve 238 is movably connected to the actuator 240 by a pair of pins 244 that extend between these two components (see FIG. 17). The selector sleeve 238 may be rotated relative to the hub 242 to linearly move the actuator 240 along the longitudinal axis A. In other words, rotational movement of the selector sleeve 238 results in linear movement of the actuator 240. The hub 242 may include tactile indicators 243 (see FIG. 17) for indicating a dimeter of the socket to be bored in bone by the blade 216.

A positioning of the inner shaft 214 is locked relative to the actuator 240 by a set screw 246, and therefore, linear movement of the actuator 240 results in linear movement of the inner shaft 214. Linear movement of the inner shaft 214 pushes the blade 216 against a slanted wall 228 of the cam cap 224 in the manner described above to move the blade 216 to the second position P2. Rotation of the selector sleeve 238 in the opposite direction retracts the blade 216 toward the first position P1.

A spring 248 is housed between the actuator 240 and a compression cap 250 that is secured to the selector sleeve 238. The spring 248 pushes against the actuator 240 as the selector sleeve 238 is turned, thus causing the actuator 240 to piston back and forth inside the selector sleeve 238 during diameter selection (i.e., during positioning of the blade 216 between the first position P1 and the second position P2).

The selector sleeve 238 may include a knurled surface 252. The knurled surface 252 is designed to improve a user's grip when turning the selector sleeve 238.

The outer tube 212 is connected to the hub 242. The hub 242 supports the selector sleeve 238 and provides for single plane rotation of the selector sleeve 238 during diameter selection.

Referring now primarily to FIGS. 17 and 18, the pins 244 may travel within a helical groove 254 formed in the actuator 240 as the selector sleeve 238 is rotated during diameter selection. Movement of the pins 244 within the helical groove 254 forces translational movement of the inner shaft 214. In an embodiment, the helical groove 254 extends along a helical path that wraps at least partially around the body of the actuator 240. Thus, the helical path of the helical groove 254 is non-linear.

In another embodiment, the helical groove 254 includes a plurality of detents 256. A ridge 258 extends between adjacent detents 256. The pins 244 must travel over the ridges 258 to move from one detent 256 to an adjacent detent 256. This may provide tactile feedback to the user of a change in the diameter setting. In an embodiment, the force required to move the pins 244 from one detent 256 to another is large enough to prevent inadvertent movement of the selector sleeve 238, and thus, the blade 216. Therefore, the detents 256/ridge 258 configuration of the helical groove 254 helps maintain the selector sleeve 238, and thus the blade 216, at a desired diameter setting during a bone cutting procedure.

The clutch assembly 218 may additionally include a connector 253. In an embodiment, the connector 253 is an integral component of the inner shaft 214. In another embodiment, the connector 253 is as a Jacobs connector. Powered equipment, such as a drill, may be connected to the connector 253 for rotating the entire expandable reamer 210 after the blade 216 has been positioned in the second position P2 to achieve a desired bore diameter in bone.

FIGS. 19-29 illustrate yet another exemplary expandable reamer 310. The expandable reamer 310 may include an outer tube 312, an inner shaft 314, a blade 316, and an actuator assembly 318. The blade 316 may be incrementally advanced between a first position P1 (see FIG. 19) and a second position P2 (see FIG. 20). The first position P1 is a non-cutting position in which the blade 316 is concealed inside the outer tube 312, and the second position P2 is a cutting position in which the blade 316 is exposed outwardly of the outer tube 312 for removing diseased bone. In an embodiment, the blade 316 may be incrementally advanced to bore a socket into bone that is any diameter. In an embodiment, the blade 316 is incrementally advanced to bore a socket into bone that is any diameter. In an embodiment, the diameter is a range between about 5 mm to about 10 mm, about 5 mm to about 15 mm, about 5 mm to about 18 mm, or about 5 mm to about 20 mm. Of course, the expandable reamer 310 could be configured to bore a socket of any size.

The outer tube 312 and the inner shaft 314 are disposed along a longitudinal axis A. The inner shaft 314 is at least partially surrounded by the outer tube 312. In an embodiment, the outer tube 312 and the inner shaft 314 are concentric relative to one another.

In another embodiment, the outer tube 312 is fixed and the inner shaft 314 is movable along the longitudinal axis A. Movement of the inner shaft 314 relative to the outer tube 312 positions the blade 316 in the second position P2 for reaming diseased tissue, as discussed in greater detail below.

Figure 21:
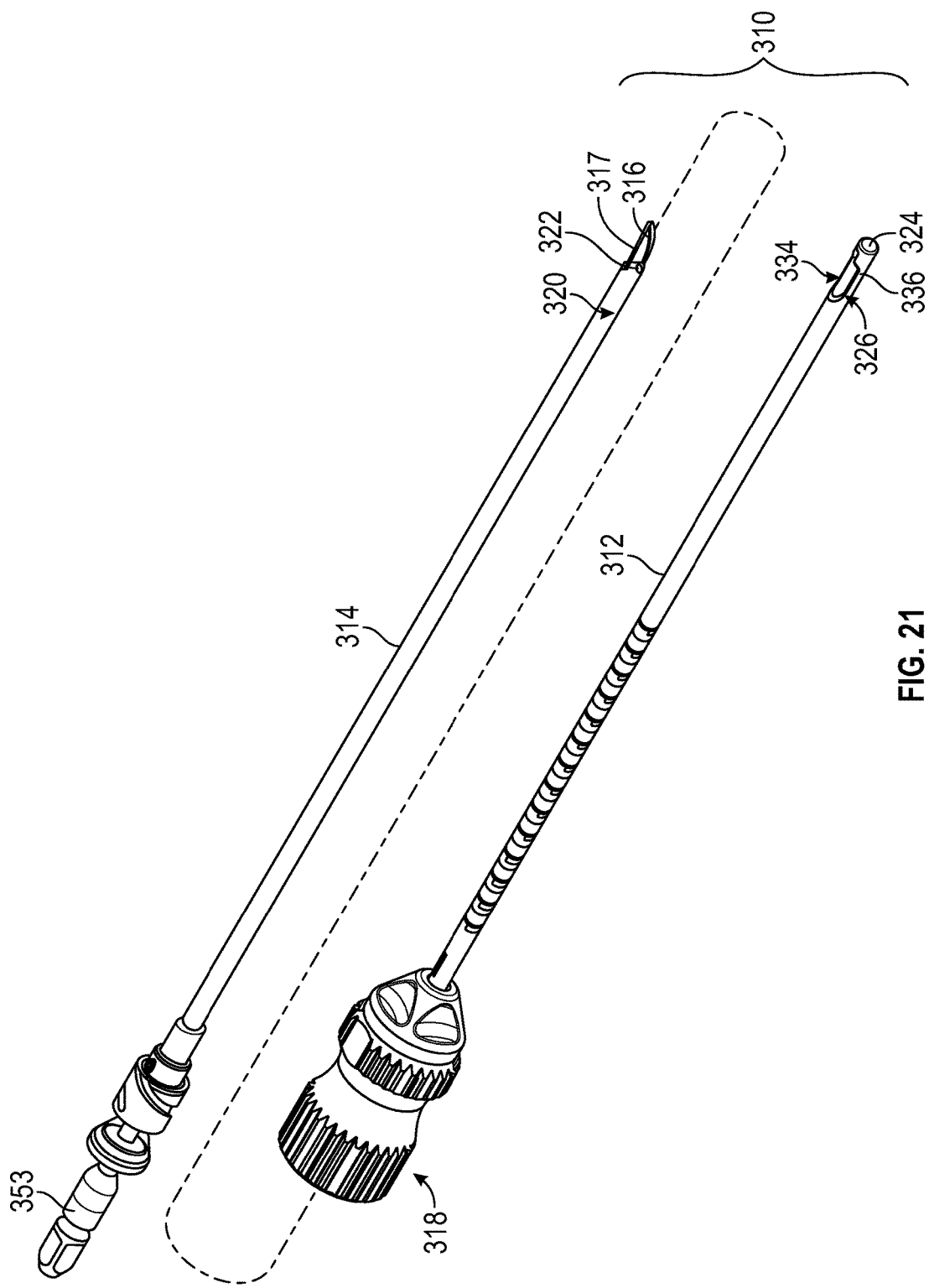
FIG. 21 is an exploded view of the expandable reamer of FIGS. 19 and 20.

The expandable reamer 310 includes a single blade 316, although additional blades could be provided within the scope of this disclosure. In an embodiment, the blade 316 is movably connected to a distal portion 320 of the inner shaft 314 by a pin 322 (i.e., the blade 316 is hinged to the inner shaft 314 as best shown in FIG. 21). The blade 316 may include one or more cutting edges 317.

A cam cap 324 is received within a distal portion 326 of the outer tube 312 for guiding movement of the blade 316 along an arced path between the first position P1 and the second position P2. The cam cap 324 is substantially similar to the cam cap 224 described above and shown in FIGS. 14 and 15 and therefore its features are not repeated here.

In an embodiment, the blade 316 is incrementally advanced through a window 334 formed through a sidewall 336 of the outer tube 312. Accordingly, in the first position P1, the expandable reamer 310 provides an atraumatic device that substantially reduces risks of inadvertent damage to surrounding tissue during the positioning of the expandable reamer 310 within bone. The blade 316 of the expandable reamer 310 may be advanced radially outward from the outer tube 312 to the second position P2 for preparing a socket in bone. In the second position P2, the blade 316 is non-parallel (i.e., transverse) to the longitudinal axis A and is exposed outside of the outer tube 312.

Figure 22:
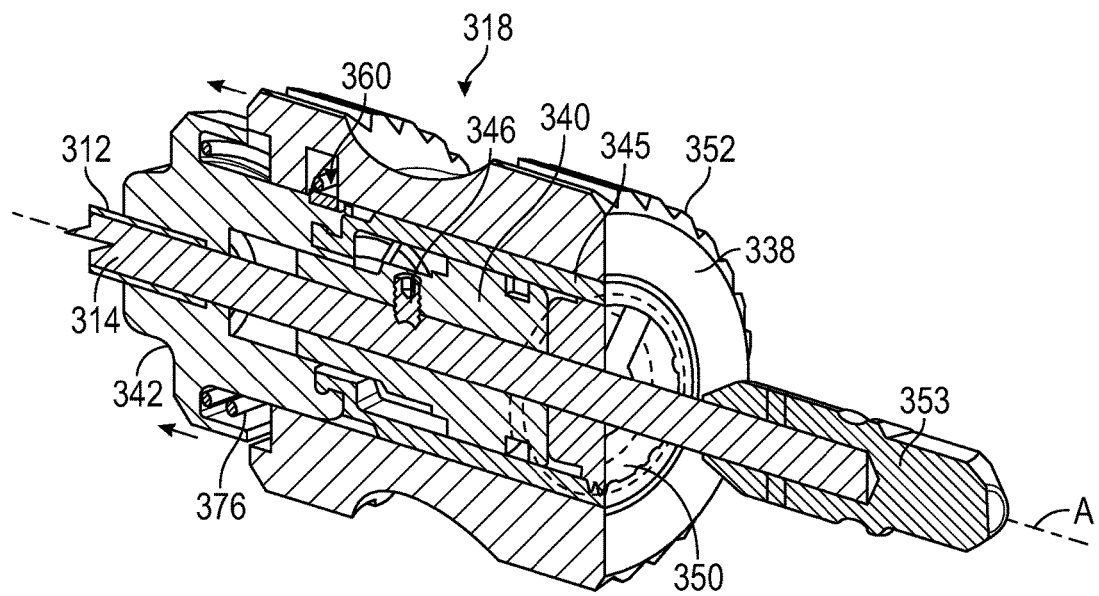
FIGS. 22, 23, and 24 illustrate an actuator assembly of the expandable reamer of FIGS. 19 and 20.
Figure 23:
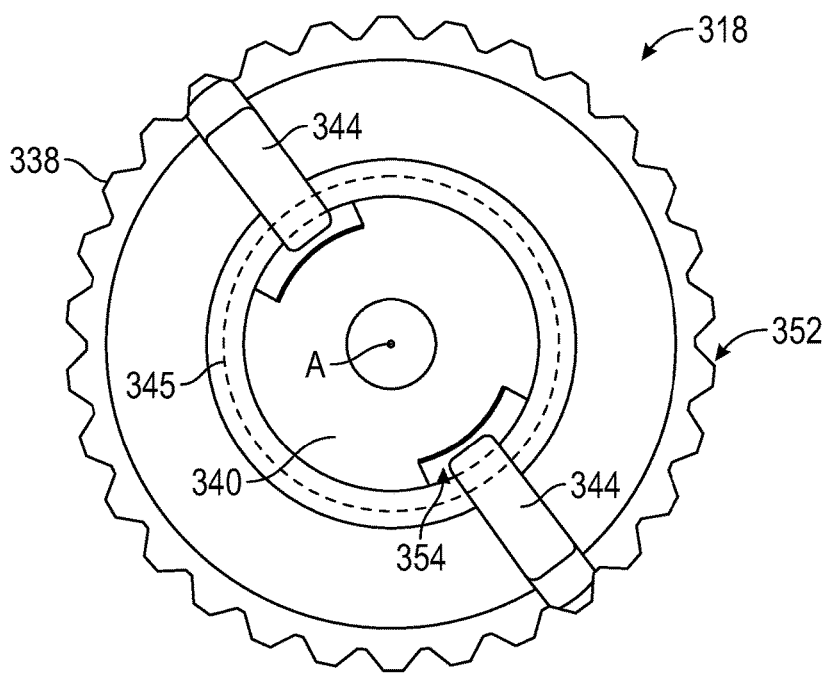
Figure 24:
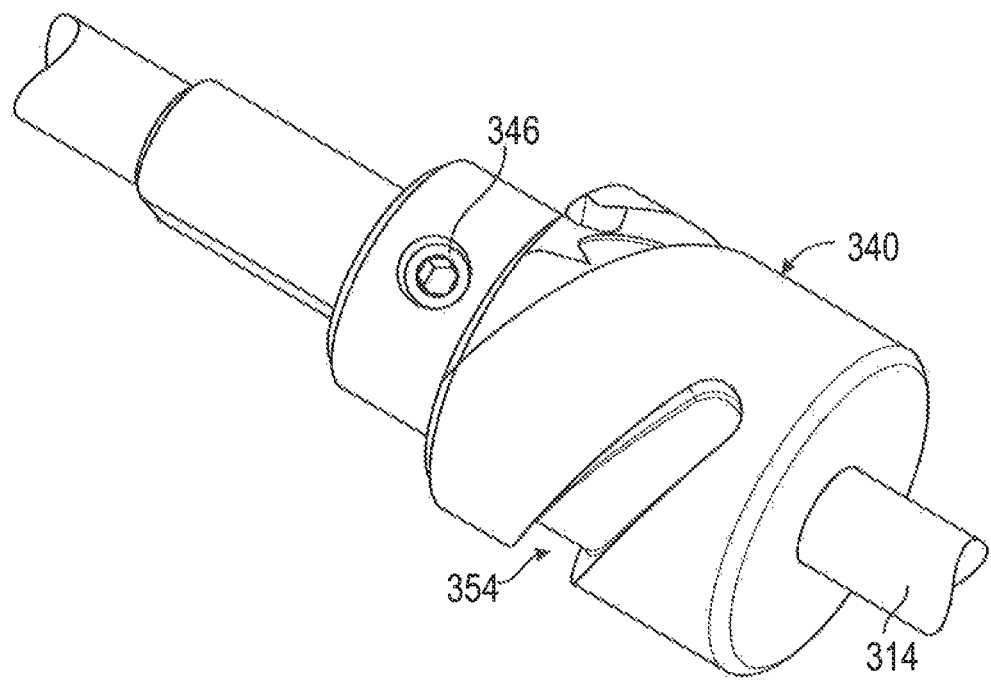
Figure 25:
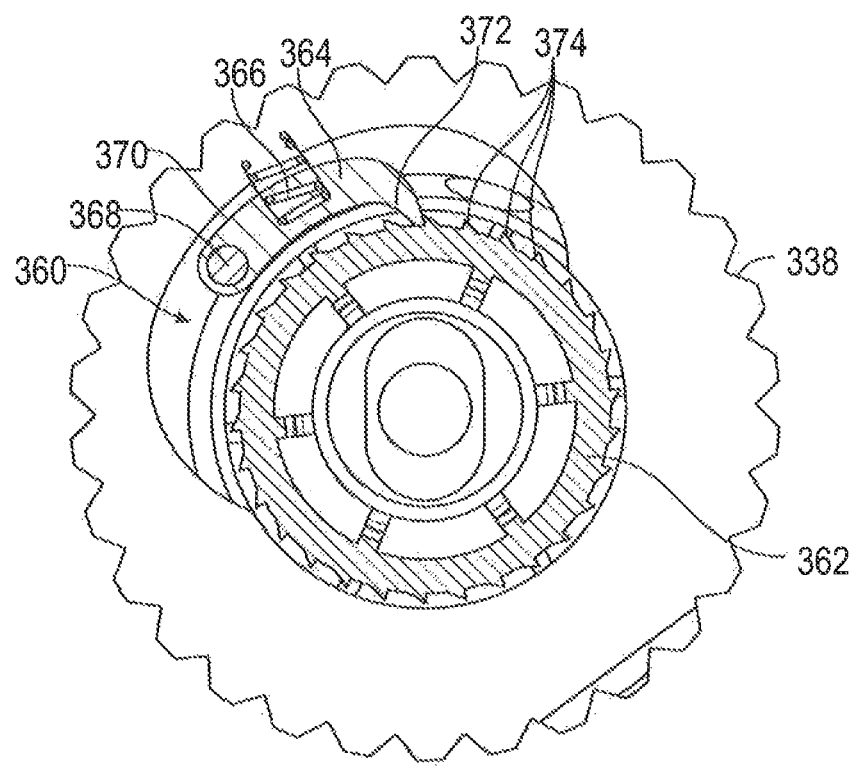
FIGS. 25, 26, 27, 28, and 29 illustrate a ratchet assembly of the expandable reamer of FIGS. 19 and 20.

The actuator assembly 318 is configured for moving the blade 316 in the manner described above. As best illustrated in FIGS. 22, 23, and 24, the actuator assembly 318 may include a selector sleeve 338, an actuator 340, and a hub 342. The selector sleeve 338 is movably connected to the actuator 340 by a pair of pins 344 (see FIG. 23). The selector sleeve 338 may be rotated relative to the hub 342 to linearly translate the actuator 340 along the longitudinal axis A. In other words, rotational movement of the selector sleeve 338 results in linear movement of the actuator 340.

In an embodiment, a snap bushing 345 rotationally connects the selector sleeve 338 to the hub 342. The snap bushing 345 may be snapped into the hub 342 and is connected to the selector sleeve 338 by the pins 344 (see FIG. 23).

Although not shown, the hub 342 could include tactile indicators for indicating a dimeter of the socket that is to be bored in bone by the blade 316.

A positioning of the inner shaft 314 is locked relative to the actuator 340 by a set screw 346, and therefore, linear movement of the actuator 340 results in linear movement of the inner shaft 314. Linear movement of the inner shaft 314 pushes the blade 316 against a slanted wall (see feature 228 of FIG. 15) of the cam cap 324 in the manner described above to move the blade 316 toward the second position P2. Rotation of the selector sleeve 338 in the opposite direction retracts the blade 316 toward the first position P1.

A stop cap 350 (see FIG. 22) is secured to the selector sleeve 338. The stop cap 350 establishes a positive stopping surface for the actuator 340 during diameter selection. In an embodiment, the stop cap 350 is removable to disassemble the actuator assembly 318.

The selector sleeve 338 may include a knurled surface 352. The knurled surface 352 is designed to improve a user's grip when turning the selector sleeve 338.

The outer tube 312 is connected to the hub 342. The hub 342 supports the selector sleeve 338 and provides for a single plane rotation of the selector sleeve 338 during diameter selection.

Referring now primarily to FIGS. 23 and 24, the pins 344 may travel within a helical groove 354 formed in the actuator 340 as the selector sleeve 338 is rotated during diameter selection. Movement of the pins 344 within the helical groove 354 forces translational movement of the inner shaft 314. In an embodiment, the selector sleeve 338 is rotated in a clockwise direction to move the inner shaft 314 forward and advance the blade 316, and is rotated in a counterclockwise direction to move the inner shaft 314 backward and retract the blade 316. In an embodiment, the helical groove 354 extends along a helical path that wraps at least partially around the body of the actuator 340. Thus, the helical path of the helical groove 354 is non-linear.

The actuator assembly 318 may additionally include a ratcheting assembly 360, which is best illustrated in FIGS. 25-29. The ratcheting assembly 360 controls the ability to rotate the selector sleeve 338.

Figure 26:
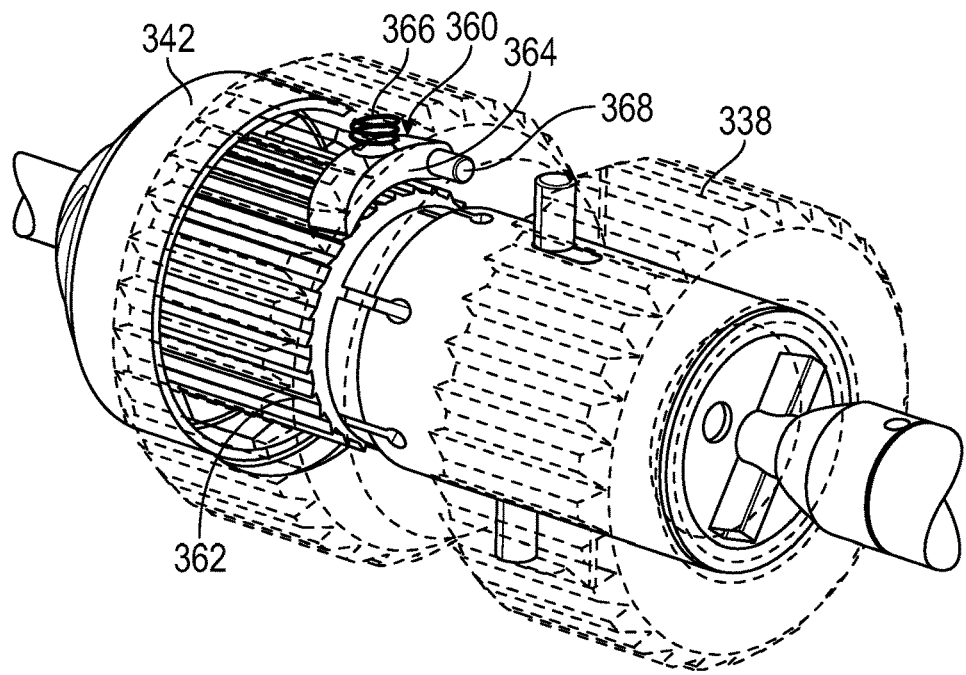
Figure 29:
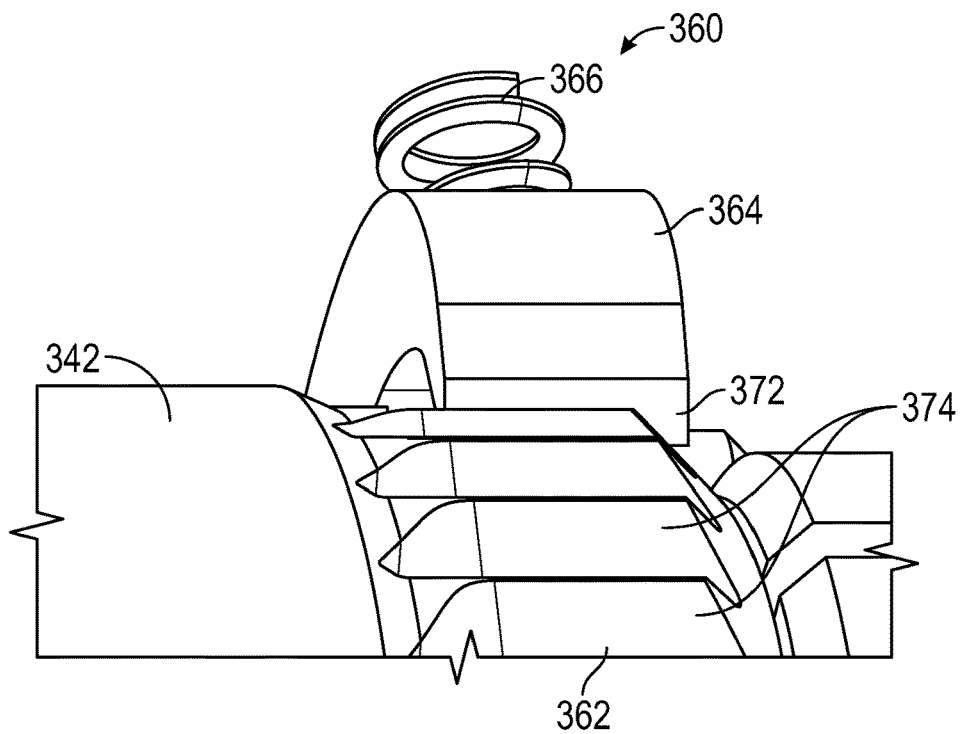

In an embodiment, the ratcheting assembly 360 includes a gear 362, a pawl 364, a spring 366, and a pin 368. The pin 368 mounts the pawl 364 within a recess 370 of the selector sleeve 338. The pawl 364 includes a projection 372 that selectively engages between teeth 374 of the gear 362 to lock a positioning of the selector sleeve 338 relative to the hub 342. The selector sleeve 338 cannot be rotated to move the blade 316 when the pawl 364 is engaged with the gear 362. The pawl 364 is biased toward the gear 362 by the spring 366. The engaged position of the pawl 364 is shown in FIGS. 26 and 29.

Figure 27:
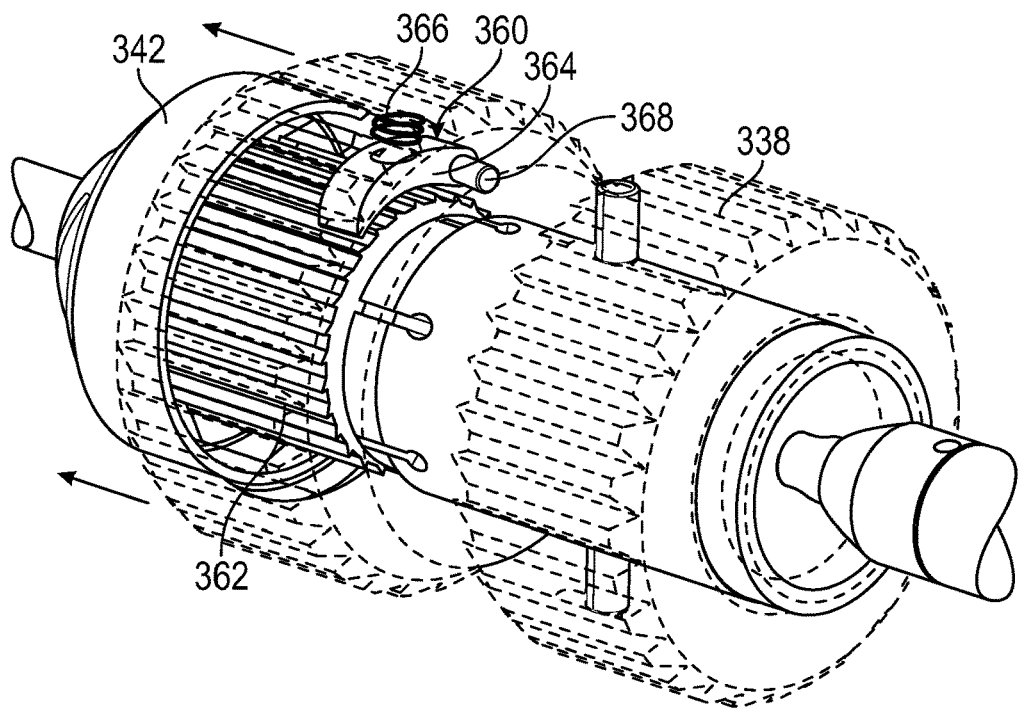
Figure 28:
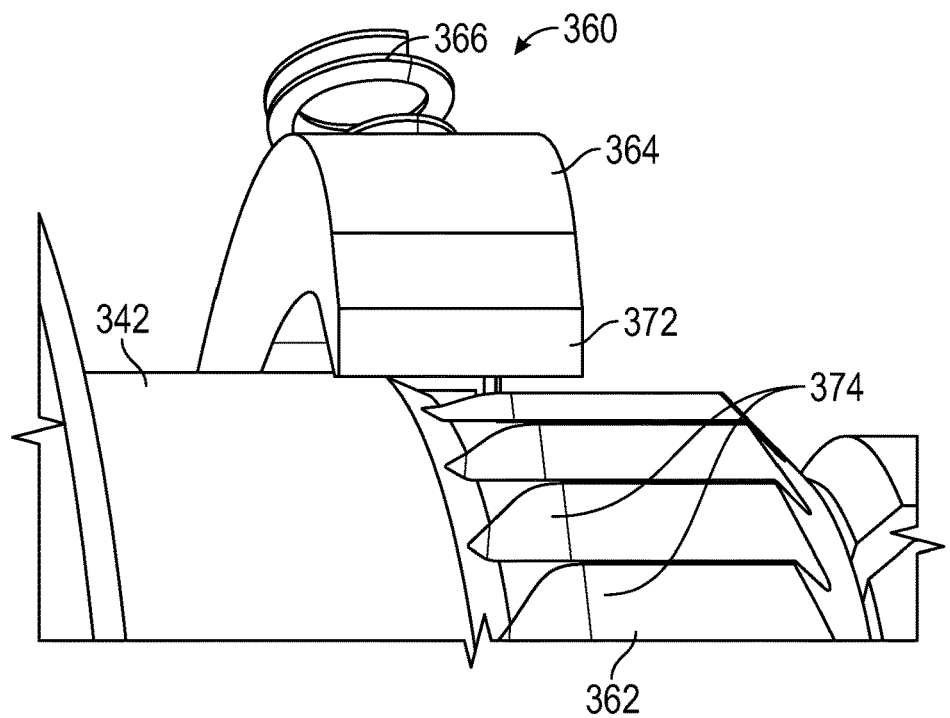

The selector sleeve 338 may be unlocked relative to the hub 342 by disengaging the pawl 364 from the gear 362. For example, the selector sleeve 338 may be pushed forward toward the hub 342, thus overcoming a biasing force of a spring 376 housed between the hub 342 and the selector sleeve 338 (see FIG. 22). As the selector sleeve 338 is moved forward, the pawl 364 is moved out of engagement with the gear 362 such that the projection 372 is no longer engaged between the teeth 374. The disengaged position of the pawl 364 is shown in FIGS. 27 and 28.

The selector sleeve 338 may then be rotated relative to the hub 342 to actuate the blade 316. Once a desired diameter has been selected and the user releases the forward force on the selector sleeve 338, the spring 376 forces the selector sleeve 338 rearward, thus forcing the pawl 364 back into engagement with the gear 362 (see FIGS. 26 and 29) and again locking the selector sleeve 338 from rotational movement. The ratcheting assembly 360 therefore substantially prevents inadvertent movement of the blade 316 once a desired diameter setting has been selected and during bone reaming.

The clutch assembly 318 may additionally include a connector 353. Powered equipment, such as a drill, may be connected to the connector 353 for rotating the entire expandable reamer 310 after the blade 316 has been positioned in the second position P2 to achieve a desired bore diameter in bone.

FIGS. 30-35 schematically illustrate a method for removing diseased bone using an expandable reamer. In these figures, the method is illustrated using the expandable reamer 310 of FIGS. 19-29; however, any of the expandable reamers described in this disclosure could be utilized in the proposed method for removing diseased bone. It should be understood that the method described herein and shown in FIGS. 30-35 could include a greater or fewer number of steps and that the steps could be performed in a different order within the scope of this disclosure.

Figure 30:
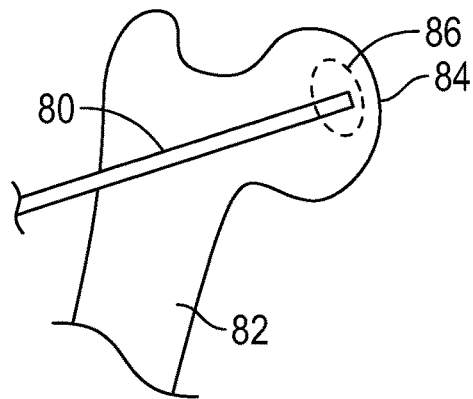
FIGS. 30, 31, 32, 33, 34, and 35 schematically illustrate an exemplary method of removing areas of diseased bone.

Referring first to FIG. 30, the method begins by inserting a guide pin 80 into a bone 82. In an embodiment, the bone 82 is a femur that includes a femoral head 84, although the method may be beneficially used elsewhere in a patient (e.g., the knee, etc.). A surgeon or other medical professional would be able to select an appropriate positioning and/or placement of the guide pin 80 and could use fluoroscopic guidance and/or a targeting guide to achieve proper placement within the bone 82.

The guide pin 80 is inserted into diseased bone 86 (e.g., a lesion). In an embodiment, the guide pin 80 is positioned such that it does not violate the articular cartilage overlying the lesion. In other words, the method may be performed subchondrally.

Figure 31:
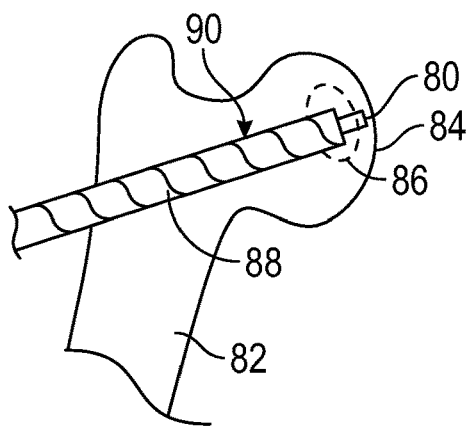

Once the guide pin 80 has been positioned, a cannulated drill bit 88 is placed over the guide pin 80 to ream a tunnel 90 (i.e., void) into the bone 82, as shown in FIG. 31. The size of the guide pin 80 and the cannulated drill bit 88 may vary depending upon the size of the patient, among other criteria. The tunnel 90 could alternatively be formed without using the guide pin 80. Once the bone 82 has been reamed, the cannulated drill bit 88 and guide pin 80 are removed.

Figure 32:
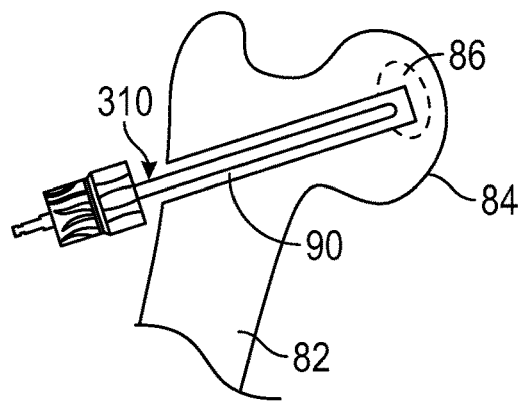

Next, as illustrated by FIG. 32, the expandable reamer 310 may be inserted into the tunnel 90 and positioned within the bone 82 such that it extends into the diseased bone 86. During positioning, the cutting blade 316 of the expandable reamer 310 is concealed inside of the outer tube 312 (see position P1 of FIG. 19).

Figure 33:
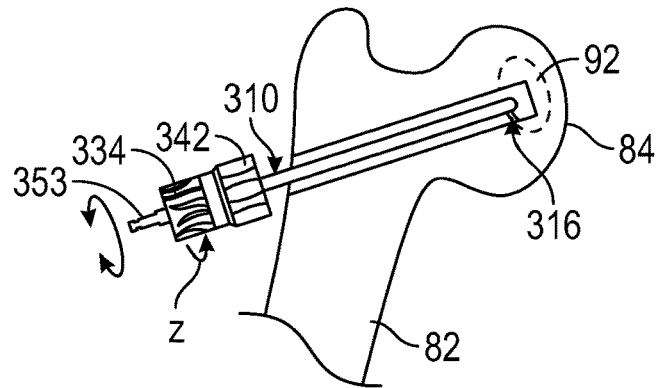

Referring now to FIG. 33, the cutting blade 316 of the expandable reamer 310 may next be incrementally moved to a cutting position. For example, the cutting blade 316 can be advanced by turning the selector sleeve 338 in the Z direction to effectuate axial movement of the inner shaft 314, which is converted to rotational movement of the blade 316 by the cam cap 324 to position the cutting blade 316 in the desired cutting position. The desired cutting position may vary depending on the amount of diseased bone 86 that is present.

Figure 34:
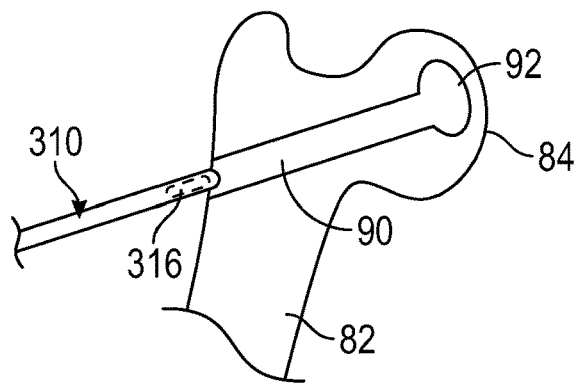

The entire expandable reamer 310 may then be rotated, such as using power equipment (not shown) that is connected to the connector 353, to create a retrograded socket 92 in the bone 82 with the blade 316, thereby removing the diseased bone 86. The cutting blade 316 may then be retracted (by disengaging the pawl 364 from the gear 362 of the ratcheting assembly 360 by moving the selector sleeve 338 forward in a direction toward the hub 342 and subsequently turning the selector sleeve 338 in an opposite direction) and the expandable reamer 310 removed from the bone 82 after the socket 92 has been adequately formed as shown in FIG. 34. The tunnel 90 and the socket 92 may be aspirated, such as with a combination of suction and irrigation, to remove any debrided tissue that may exist after reaming.

Figure 35:
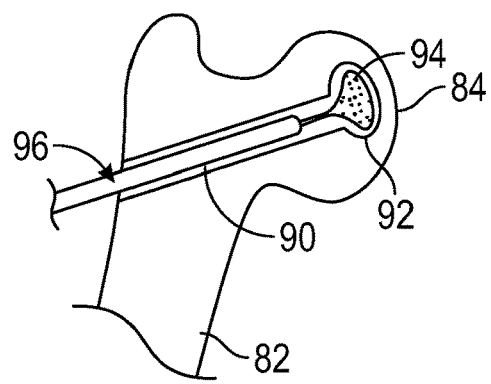

Finally, as shown in FIG. 35, the tunnel 90 and the socket 92 may be backfilled with a biologic 94. In an embodiment, the biologic 94 includes bone marrow concentrate (BMC) or BMC mixed with demineralized bone matrix (DBM). In another embodiment, the biologic 94 is injected with a delivery cannula 96 working from the socket 92 backwards toward the tunnel 90. In yet another embodiment, the tunnel 90 and the socket 92 are completely filled with the biologic 94.

The expandable reamers of this disclosure are atraumatic surgical devices that substantially reduce the risks of inadvertent damage to surrounding tissue during the positioning of the expandable reamers within bone. The blades of the expandable reamers may be incrementally positioned to achieve a multitude of socket diameters using novel actuator assemblies.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:
1. An expandable reamer, comprising:
 an outer tube;
 an inner shaft within the outer tube;
 a blade connected to the inner shaft and movable between a first position in which the blade is inside the outer tube and a second position in which the blade is exposed outside of the outer tube;
 a cam cap configured to guide movement of the blade outwardly of the outer tube; and an actuator assembly configured to move the blade between the first position and the second position, the actuator assembly including:
a selector sleeve;
an actuator;
a first pin connected to the selector sleeve and movable within a helical groove of the actuator to linearly translate either the inner shaft or the outer tube as the selector sleeve is rotated; and
a ratcheting assembly that includes an engaged position in which the selector sleeve is prevented from rotating and a disengaged position in which the selector sleeve is free to rotate;
wherein a pawl of the ratcheting assembly engages a gear in the engaged position and is released from the gear in the disengaged position.

2. An expandable reamer, comprising:
an outer tube;
an inner shaft within the outer tube;
a blade connected to the inner shaft and movable between a first position in which the blade is inside the outer tube and a second position in which the blade is exposed outside of the outer tube; and
an actuator assembly configured to move the blade between the first position and the second position, the actuator assembly including a selector sleeve, an actuator, and a first pin connected to the selector sleeve and movable within a groove of the actuator to linearly translate either the inner shaft or the outer tube as the selector sleeve is rotated.

3. The expandable reamer as recited in claim 2, comprising a cam cap configured to guide movement of the blade outwardly of the outer tube.

4. The expandable reamer as recited in claim 3, wherein the cam cap is positioned within a distal portion of the outer tube.

5. The expandable reamer as recited in claim 3, wherein the cam cap includes a slanted wall that guides the blade along an arced path as the blade is moved between the first position and the second position.

6. The expandable reamer as recited in claim 5, comprising grooved tracks disposed on each side of the slanted wall, and the blade includes projections that are guided within the grooved tracks.

7. The expandable reamer as recited in claim 2, wherein the blade is hinged to a distal portion of the inner shaft.

8. The expandable reamer as recited in claim 2, wherein the groove is a helical groove.

9. The expandable reamer as recited in claim 8, wherein the helical groove includes a plurality of detents.

10. The expandable reamer as recited in claim 9, wherein the first pin is movable from a first detent of the plurality of detents to a second detent of the plurality of detents to alter a cutting diameter of the blade.

11. The expandable reamer as recited in claim 10, comprising a ridge disposed between the first detent and the second detent.

12. The expandable reamer as recited in claim 2, comprising a ratcheting assembly for locking the selector sleeve from rotational movement.

13. The expandable reamer as recited in claim 12, wherein the ratcheting assembly includes an engaged position in which the selector sleeve is prevented from rotating and a disengaged position in which the selector sleeve is free to rotate.

14. The expandable reamer as recited in claim 13, wherein the ratcheting assembly includes a pawl and a gear, and the pawl engages the gear in the engaged position and is released from the gear in the disengaged position.

15. The expandable reamer as recited in claim 13, wherein the selector sleeve is movable longitudinally forward to move the ratcheting assembly from the engaged position to the disengaged position.

16. The expandable reamer as recited in claim 2, wherein the outer tube and the inner shaft are disposed along a longitudinal axis, and the blade is parallel to the longitudinal axis in the first position and transverse to the longitudinal axis in the second position.

17. A method for removing diseased bone, comprising:
incrementally advancing the blade of the expandable reamer of claim 2 to a cutting position relative to the diseased bone by rotating the selector sleeve of the expandable reamer;
wherein, as the selector sleeve is rotated, the first pin of the selector sleeve travels within the groove of the actuator to linearly translate the actuator.

18. The method as recited in claim 17, comprising rotating the expandable reamer with the blade in the cutting position to remove the diseased bone.

19. The method as recited in claim 17, comprising reaming a tunnel into a bone that includes the diseased bone prior to positioning the expandable reamer, and then backfilling the tunnel with a biologic after removing the diseased bone.

20. The method as recited in claim 17, wherein incrementally advancing the blade includes moving the blade along an arced path to a position radially outward from the outer tube of the expandable reamer.

* * * * *